United States Patent [19]

Carver et al.

[11] Patent Number: 5,256,801
[45] Date of Patent: Oct. 26, 1993

[54] PROCESSES OF CONVERTING TAXANES INTO 10-DEACETYLBACCATIN III

[75] Inventors: David R. Carver; Timothy R. Prout, both of Boulder; Hernita A. Ewald, Denver; Donia L. Henderson, Boulder, all of Colo.

[73] Assignee: NaPro BioTherapeutics, Inc., Boulder, Colo.

[21] Appl. No.: 986,852

[22] Filed: Dec. 4, 1992

Related U.S. Application Data

[63] Continuation-in-part of Ser. No. 930,840, Aug. 14, 1992, Pat. No. 5,202,448.

[51] Int. Cl.$^5$ .......................................... C07D 305/14
[52] U.S. Cl. ............................................... 549/510
[58] Field of Search ........................................ 549/510

[56] References Cited

PUBLICATIONS

J. Org. Chem., vol. 51, pp. 3239–3242, No. 16, 1986.
Journal of Natural Products, vol. 53, The Chemistry of Taxol, a Clinically Useful Anticancer Agent, pp. 1–12, No. 1, Jan.–Feb. 1990.
J.C.S. Chem. Comm., Structures of Some Taxane Diterpenoids, Baccatins—III, —VI, —VI, and —VII and 1—Dehydroxybaccatin—IV, Possessing and Oxetan Ring, pp. 365–366, 1975.
Tetrahedron, vol. 42, F. Gueritte-Voegelein, V. Senilii, B. David, D. Guenard and P. Potier, Chemical Studies of 10–Deacetyl Baccatin III, Hemisynthesis of Taxol Derivatives, pp. 4451–4460, No. 16, 1986.

*Primary Examiner*—Marianne M. Cintins
*Assistant Examiner*—Michael B. Hydorn
*Attorney, Agent, or Firm*—Timothy J. Martin; Dana S. Rewoldt

[57] ABSTRACT

A process for the preparation of a compound of formula (I)

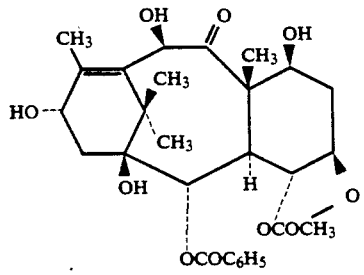

comprising contacting a mixture containing at least one taxane compound having an ester linkage at the C-13 position with at least one borohydride reducing salt in a reaction solvent in the presence of a Lewis acid.

11 Claims, No Drawings

PROCESSES OF CONVERTING TAXANES INTO 10-DEACETYLBACCATIN III

The present invention is a continuation-in-part of our prior application identified as Ser. No. 07/930,840 filed Aug. 14, 1992, now U.S. Pat. No. 5,202,448.

FIELD OF THE INVENTION

The present invention relates to a process of converting partially purified taxane mixtures into baccatin III or 10-deacetylbaccatin III. Specifically, the present invention relates to a process using borohydride reducing salts in the presence of Lewis acids to convert 10-deacetyltaxol, cephalomannine, taxol and other taxanes into related baccatins.

BACKGROUND OF THE INVENTION

Taxol, (1)

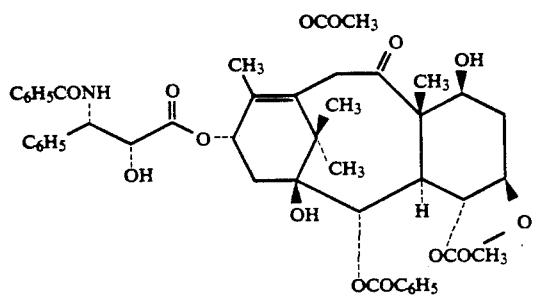

is a diterpenoid found in the Western Yew, (*Taxus brevifolia*). Taxol has shown excellent anticancer activity in clinical trials. However, extensive testing of taxol has been difficult because it is extracted from a natural vegetation that is in short supply. To avoid depletion of the plant life that contains taxanes total synthesis of taxol has been attempted, but so far these attempts have been unsuccessful. However, significant strides have been made in the semi-synthesis of taxol from other naturally occurring taxanes such as baccatin III and 10-deacetylbaccatin III. At least three different methods of converting baccatin III and 10-deacetylbaccatin III into taxol have been reported.

The structure of baccatin III (2)

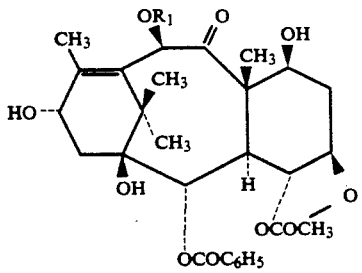

has the basic diterpenoid structure of taxol without the side chain at the C-13 position and with $R_1=COCH_3$. The structure of 10-deacetylbaccatin III is similar to the structure above except at the C-10 position $R_1=H$. Thus, due to the basic diterpene structure, baccatin III and the other related baccatins such as 10-deacetylbaccatin III are important starting materials in taxol semi-synthesis. The significance of baccatin III and 10-deacetylbaccatin III is expected to increase as more taxol cancer testing is performed. Already it appears that water soluble taxol-like compounds with slightly modified C-13 side chains may be more desirable as cancer drugs than the natural occurring, less soluble, taxol. This increases the unresolved need for baccatin III and 10-deacetylbaccatin III as a starting material to synthesize taxol and second and third generation taxol-like compounds.

The present source of baccatin III and 10-deacetylbaccatin III is an extraction from natural vegetation containing taxanes such as the English Yew (*Taxus baccatta*). The supply of these raw materials is limited. Conversion of taxol and cephalomannine into baccatin III is a viable method of increasing the supply of baccatin III. The conversion of 10-deacetyltaxol and other taxanes into 10-deacetylbaccatin III is a viable method of increasing the supply of 10-deacetylbaccatin III.

Miller reported that cephalomannine was converted in a 19% yield to baccatin III by methanolysis in the presence of sodium bicarbonate. See, *Journal of Organic Chemistry*, Volume 46, pp. 1469-1474 (1984). Preparation of a 97% yield of baccatin III from pure taxol was reported by Magris et al. See, "Modified taxols, 3. Preparation and Acylation of Baccatin III", *Journal of Organic Chemistry*, Vol. 51, pp. 3239-3242, 1986. The preparation of baccatin III according to the Magris, et al. process was performed as follows: a 100 mg sample of pure taxol in dry $CH_2CL_2$ (2.0 mL) was allowed to react with $Bu_4NBH_4$ (50 mg) for one hour, and the reaction was quenched with 0.5 mL of AcOH. The mixture was stirred ten minutes, evaporated, and the product isolated by preparative TLC. This process was reported to give a 97% yield of baccatin III from pure taxol.

The Magris, et al. paper also indicated that when this same reaction was run on a starting material consisting of an unpurified taxol/cephalomannine mixture instead of pure taxol, the result was a reduced yield of baccatin III. High yield conversion of pure taxol to baccatin III is extremely useful in the laboratory where pure taxol is available. However, there is a need for a high yield process to convert crude taxane mixtures (containing taxol/cephalomannine and other taxanes) into baccatin III and 10-deacetylbaccatin III.

In the commercial extraction of taxol from yew tree material, significant quantities of taxanes including taxol, 10-deacetyltaxol and cephalomannine are generated. These mixtures contain useful taxanes (which are thrown away as by-products during the purification of taxol). The Magris, et al. process has not demonstrated particularly high yield results when partially purified mixtures containing low percentages of taxol, 10-deacetyltaxol and cephalomannine are converted into baccatin III or 10-deacetylbaccatin III.

In large scale processing of taxol for commercial use, the cost associated with achieving the Magris, et al. yield is not economically feasible. The Magris, et al. process uses tetrabutylammonium borohydride, an expensive reducing salt. Furthermore, this procedure is run at 0° C. which adds refrigeration costs to the final product. Most taxane extraction processes result in by-products containing some taxol, 10-deacetyltaxol, cephalomannine and significant amounts of other substances. Therefore, there remains a need for a high yield inexpensive process of converting these partially purified mixtures of taxanes including but not limited to taxol, 10-deacetyltaxol and/or cephalomannine into baccatin III or 10-deacetylbaccatin III.

SUMMARY OF THE INVENTION

An object of the present invention is to convert partially purified organic by-products of the taxane extraction process into 10-deacetylbaccatin III.

A further object of the present invention is to provide a simple, method of preparing 10-deacetylbaccatin III at room temperature.

Still a further object is to provide an inexpensive method of converting a partially purified mixture of taxol, cephalomannine, 10-deacetyltaxol and other substances into baccatin III or 10-deacetylbaccatin III.

This invention provides a process for the preparation of 10-deacetylbaccatin III by contacting a mixture containing at least one taxane compound having an ester linkage at the C-13 position with at least one borohydride reducing salt in a reaction solvent in the presence of a Lewis acid. The preferred reaction solvent is tetrahydrofuran (an apolar, donor solvent). Triglyme converted approximately a third of the 10-deacetyltaxol into 10-deacetylbaccatin III. Glyme in the presence of cobalt chloride gave a 21% yield of 10-deacetylbaccatin III. Methylene chloride in the presence of tin chloride resulted in a 24% yield of 10-deacetylbaccatin III. The preferred Lewis acids are metal halides such as tin(II) chloride or cobalt(II) chloride.

This invention further provides a process of preparing 10-deacetylbaccatin III by contacting a mixture containing at least one taxane compound constituent having an ester linkage at the C-13 position in a triglyme reaction solvent with a borohydride reducing salt. The members of the glyme family including $CH_3(OCH_2CH_2)_xOCH_3$ where x equals integers 1-5 could be substituted for triglyme. Glyme and diglyme are expected to convert less material to 10-deacetylbaccatin III than triglyme.

DESCRIPTION OF THE PRESENT INVENTION

The present invention relates to high yield processes for converting partially purified mixtures of taxanes containing taxol, 10-deacetyltaxol and cephalomannine into 10-deacetylbaccatin III. The Magris, et al. paper reported that their process had been run on a partially purified taxane mixture containing taxol and cephalomannine, however, the baccatin III yield from this mixture was only reported as "good". The Magris et al. paper did not report any attempt to use the Magris et al. process on a taxane mixture containing 10-deacetyltaxol. Therefore, as a baseline by which to compare the present invention, the Magris, et al. process was run on a mixture of taxanes which contained 10-deacetyltaxol along with taxol, cephalomannine, baccatin III and 10-deacetylbaccatin III. In this experiment, the Magris, et al. process was performed at 0° C. on 51 mg of a dry partially purified taxane mixture containing 3.5% taxol, 2.3% cephalomannine, 1.73% 10-deacetyltaxol and 5.74% 10-deacetylbaccatin III (as determined by HPLC). The procedure was run for sixteen hours on this material in dichloromethane, with tetrabutylammonium borohydride as the reducing salt. The yield of 10-deacetylbaccatin III from the mixture was −375.00%. The negative yield indicates not only the decomposition of 1.21 mg of the 10-deacetyltaxol but also the decomposition of 3 mg of 10-deacetylbaccatin III in the starting material. This is a significant loss of material. This −375.00% yield is therefore the baseline by which the following examples can be compared.

The preferred embodiment of the present invention includes contacting a mixture containing some taxanes with a borohydride reducing salt in a reaction solvent in the presence of a Lewis acid in less than and up to stoichiometric quantities. In the preferred process sodium borohydride is employed due to the higher cost associated with the use of tetrabutylammonium borohydride. The preferred Lewis acids are compounds such as metal halides. The test to determine the viability of a Lewis acid is two-fold. One, the Lewis acid should covalently bond with strong nucleophiles and second, the Lewis acid should not react with the borohydride to form boranes. Magnesium chloride (which is not expected to covalently bond with strong nucleophiles) was tested and did not produce 10-deacetylbaccatin III. More covalent Lewis acids such as $SnCl_2$ and $CoCl_2$ increased the 10-deacetylbaccatin III yield significantly above the baseline yield of the Magris et al. procedure.

The types of borohydride reducing salts, reaction solvents and Lewis acids used in the alternative embodiments of the present invention have been selected to result in a commercially viable process of converting certain into 10-deacetylbaccatin III while other taxanes are converted into baccatin III.

The processes of the present invention yield a higher percentage of 10-deacetylbaccatin III from a taxane mixture at room temperature than the baseline Magris, et al. process yields at 0° C. The processes of the present invention employ different reaction solvents and different Lewis acids to increase the yield of 10-deacetylbaccatin III from a starting material formed of partially purified taxanes.

In the first embodiment of the present invention, a 52% yield of 10-deacetylbaccatin III was prepared by mixing the starting material with the reaction solvent tetrahydrofuran (THF), and the reducing borohydride salt sodium borohydride. The starting material contained 3.5% taxol, 2.3% cephalomannine, 0.69% 10-deacetylbaccatin III, 1.3% 10-deacetyltaxol and other substances. A 52% yield of 10-deacetylbaccatin III at room temperature after a reaction time of 72 hours was achieved. In my related application, this same process converted a large percentage of taxol into baccatin III.

In the second embodiment of the present invention, 10-deacetylbaccatin III was prepared by contacting a starting material, having 0.69% 10-deacetylbaccatin III and 1.31% 10-deacetyltaxol, in dichloromethane and 0.1% $SnCl_2$, with sodium borohydride at room temperature. After 120 hours of reaction, 10-deacetylbaccatin III was produced in a 24% yield by HPLC analysis. The advantage of using sodium borohydride as the reducing salt over using tetrabutylammonium borohydride is primarily the expense. The former being about $0.11 a gram, while the later is $1.00 a gram. Although the Magris, et al. reference describes use of sodium borohydride to convert a pure taxol to baccatin III, this borohydride reducing salt was used with propanol and resulted in the undesired epimerization at the C-7 position. Magris, et al. therefore abandoned the sodium borohydride and used the more expensive tetrabutylammonium borohydride in association with dichloromethane to get the 97% yield of baccatin III from pure taxol.

As noted in the Magris, et al. paper, the borohydrides used in forming baccatin III are believed to be reducing esters by delivery of a hydride ion to the ester carbonyl group. This reference did not provide a solution to the decrease in the ability of the reactions to cleave the ester when the reactive borohydride reducing salt (especially if tetrabutylammonium borohydride is employed) was in contact with protic compounds. This is a substantial problem because a variety of protic compounds such as water and alcohols are found in partially purified taxane starting materials. Some of these protic substances are naturally occurring in the plant material (Taxus) and some are added in the various extraction and purification steps. Additionally, hydroxide and alkoxide basic ions may be present. These materials cause undesired epimerization and cleavage and can result in substantially decreased yields of baccatin III and likewise appear to result in the decomposition of both 10-deacetylbaccatin III and 10-deacetyltaxol.

To counteract the effects of these undesirable compounds in the starting material, the preferred embodiment of the present invention includes the addition of Lewis acids to the reaction in less than and up to stoichiometric quantities. The metal halides $SnCl_2$ and $CoCl_2$ have proven especially useful Lewis acids in this process. These metal halides in the presence of oxygen anions rapidly react to make metal oxides with the subsequent release of nontaxane reacting $Cl^-$ anions. Thus, many undesirable components of the starting material are effectively neutralized, allowing the borohydride to react more specifically with taxanes in the mixture.

In the third embodiment, 7% cobalt chloride (based on the taxol in the starting material) was added to the reaction solvent, $CH_3OCH_2CH_2OCH_3$ (glyme) and contacted with sodium borohydride at room temperature for 144 hours. This process resulted in a 21% yield of 10-deacetylbaccatin III. A low positive yield of 10-deacetylbaccatin III was also obtained in a similar experiment using 0.1% $SnCl_2$.

In the fourth preferred embodiment of the present invention, a 37% yield of 10-deacetylbaccatin III was prepared by contacting a taxane mixture starting material containing 3.5% taxol, 2.3% cephalomannine, 0.69% 10-deacetylbaccatin III and 1.3% deacetyltaxol in the reaction solvent $CH_3(OCH_2CH_2)_3OCH_3$ (triglyme) with sodium borohydride. The reaction was run at room temperature for one hundred and forty-four hours. This reaction did not require the addition of a Lewis acid to give a positive conversion of 10-deacetyltaxol to 10-deacetylbaccatin III. In fact, only 29% of the 10-deacetyltaxol was used and there was a 37% increase in the 10-deacetylbaccatin III. It appears that material other than just the 10-deacetyltaxol is being cleaved to produce the 10-deacetylbaccatin III. The specific identity of these other compounds which are being converted has not at this time been established.

The following non-limited examples provide specific processes for preparing 10-deacetylbaccatin III from a partially purified taxane mixture or purified taxane samples. All scientific and technical terms have the meanings as understood by one with ordinarily skill in the art. HPLC in the following examples was carried out on an apparatus consisting of a Spectra Physics 8800 Ternary Pump, a Rheodyne hand injector Spectra Physics SP8780 (auto-sampler), an SP4400 Chromjet integrator and a Spectra-100 (variable wavelength detector). $^1$H-NMR spectra were obtained using a Varian VXR 300S MHz spectrometer. Elemental analysis was performed by Huffman Laboratories (Golden, Colorado). Various methods of purifying the 10-deacetylbaccatin III produced by the present invention are known and understood by those skilled in the art and the purification method presented in the Examples solely listed by way of example and is not intended to limit the invention.

EXAMPLE I

Prior Art

TABLE Ia

| The reaction conditions in Example I are as follows: | |
|---|---|
| Reaction solvent | $CH_2Cl_2$ |
| Reaction temperature (degrees C.) | 0 |
| Reaction time | 16 hours |
| Reducing salt | tetrabutylammonium borohydride |
| Addtional reagents | none |

69 mg of taxanes (starting material) having 47.04% taxol, 1.04% cephalomannine, 1.73% 10-deacetyltaxol, 5.7% 10-deacetylbaccatin III was stirred into 2.0 mL dichloromethane in a 25 mL round bottom flask under a nitrogen gas atmosphere. After cooling the solution to 0° C. in an ice bath, 25 mg of tetrabutylammonium borohydride was added. The mixture was allowed to stir for one hour and the reaction was quenched by addition of 0.5 mL of AcOH.

The organic solution presumed to contain 10-deacetylbaccatin III was poured into 25 mL/g of 50% by volume acetic acid/$H_2O$. The organic solution was repeatedly extracted with an immiscible organic solvent. In this instance dichloromethane was used. The organic phase was collected and dried over anhydrous sodium sulfate. The organic phase was removed in vacuo to form a viscous oil. The residue was purified by flash chromatography on silica gel using nitrogen pressure eluting with dichloromethane/5% methanol. The selected fractions were evaporated to dryness under reduced pressure (20 mm Hg).

The dry organic material was recrystallized from a 15% solution of methanol/$H_2O$(80/20). No 10-deacetylbaccatin III was produced. In fact, 3 mg of 10-deacetylbaccatin III was lost as was 0.6 mg of 10-deacetyltaxol. The yield was a negative $(-)375.00\%$ (negative). This yield takes into account the lost material.

TABLE Ib

| Starting material (mg) | 69.0 |
|---|---|
| % 10-deacetyltaxol | 1.73 |
| 10-deacetyltaxol weight (mg) | 1.19 |
| % 10-deacetylbaccatin III | 5.74 |
| 10-deacetylbaccatin III weight (mg) | 3.96 |
| Theoretical yield 10-deacetylbaccatin III (from 10-deacetyltaxol in mg) | .800 |
| Actual yield | .96 |
| 10-deacetylbaccatin III (mg) | (−3.00) |
| % yield 10-deacetylbaccatin III (with respect to 10-deacetyltaxol) | −375.00 |
| 10-deacetyltaxol remaining (mg) | .520 |
| % 10-deacetyltaxol used | 56.300 |

EXAMPLE II

The reaction conditions in Example II are as follows:

TABLE IIa

| Starting material (sm) | 10 g |
|---|---|
| Taxol in starting material | 350 mg |
| % taxol in starting material | 3.5% |
| 10-deacetyltaxol in starting material | 131 mg |
| % 10-deacetyltaxol in starting material | 1.3% |
| Reducing salt | NaBH4 10:1 |

TABLE IIa-continued

| | |
|---|---|
| Additional reagents | SnCl$_2$ (.1%) |

10 g of taxane (starting material) containing taxol (3.5%), 10-deacetyltaxol (1.3%), 10-deacetylbaccatin III (0.6%) was stirred into 200 mL of THF in a 500 mL round bottom flask under a nitrogen gas atmosphere. Sodium borohydride in a 10:1 stoichiometric ratio based on the starting material and 0.1% tin chloride (based on molar % of taxol in the starting material) were added to the mixture. The reaction was allowed to run at room temperature for seventy-two hours. After this period, the organic solution containing the baccatin III and the 10-deacetylbaccatin III was purified by the following method. The organic solution was poured into 10 mL per gram of 50% by volume acetic acid/H$_2$O. The organic solution was then repeatedly extracted with an immiscible organic solvent, in this case THF. The organic phase was collected, dried over anhydrous sodium sulfate, and evaporated in vacuo to a viscous oil. This oil was purified by flash chromotography eluting with dichloromethane/5% methanol. The selected fractions were then reduced to dryness under reduced pressure (20 mm mercury). The dry organic material was then recrystallized from methanol. 115 mg of 10-deacetylbaccatin III were recovered resulting in a 52% yield. The $^1$NMR analysis and melting point of the product matched those previously reported for 10-deacetylbaccatin III.

TABLE IIb

| | |
|---|---|
| Reaction Solvent | THF |
| with | NaBH$_4$ |
| Reaction temp C. | room temperature |
| Reaction time | 72 hours |
| Theoretical yield 10-deacetylbaccatin III | 88 mg |
| Actual yield 10-deacetylbaccatin III (hplc) | 115 mg |
| % yield 10-deacetylbaccatin III | 52% |
| 10-deacetyltaxol remaining (hplc) | 10 mg |
| % 10-deacetyltaxol converted | 92% |

In contrast, the same procedure as described in Example II was run on 10 grams of starting material having the same taxol and 10-deacetyltaxol percentages. The reaction solvent used was dichloromethane (as was used in the Magris, et al. procedure). The 10-deacetylbaccatin III yield was only 24%, 90 mg (a lower yield resulted from larger amounts of material) as analyzed by TLC. there as 69 mg of 10-deacetyltaxol remaining; 47% of the 10-deacetyltaxol was converted. Based on TLC analysis, the reaction in dichloromethane was run for one hundred twenty hours versus seventy-two hours.

The resulting 10-deacetylbaccatin III had the following characteristics, the melting point and elemental analysis for C$_{29}$H$_{36}$O$_{10}$ (done by Huffman Laboratories, Golden, Colorado) for the product matched those reported previously for 10-deacetylbaccatin III.

The proton nuclear magnetic resonance spectrum (300 MHz; deuterated chloroform; chemical shift in ppm; coupling constants J in Hz): 1.10 (s,6H), 1.74 (s,3H), 2.06 (s,3H), 2.29 (s,3H), 2.57 (m,1H), 4.00 (d, J=7.0, 1H), 4.17 (d, J=9.0, 1H), 4.20 (m,1H), 4.32 (d, J=9.0, 1H), 4.80 (br t, 1H), 4.96 (dd, J=8.7, 1.2; 1H), 5.24 (s, 1H), 5.63 (d, J=7.0, 1H), 7.49 (t, J =7.32, 2H), 7.62 (t, J=7.57, 1H), 8.11 (d, J=7.32, 2H).

EXAMPLE III

The reaction conditions and starting material in Example III are as follows:

TABLE IIIa

| | |
|---|---|
| Starting material (mass) | 10 g |
| Taxol in starting material | 350 mg |
| % taxol in starting material | 3.5% |
| 10-deacetyltaxol in starting material | 131 mg |
| % 10-deacetyltaxol in starting material | 1.3% |
| Reducing salt | NaBH$_4$ (pellets) 10:1 |
| Additional reagents | CoCl$_2$ (7%) |

10 g of taxane starting material containing a taxol (3.5%) and cephalomannine (2.3%) was stirred into 200 mL of glyme in a 500 mL round bottom flask under a nitrogen gas atmosphere. Sodium borohydride (10:1 stoichiometric ratio based on starting material) and 7% cobalt chloride (based on the molar percent of taxol in the starting material) were added to the reaction, in pellet form. The reaction was allowed to run at room temperature for one hundred forty-four hours. After the one hundred forty-four hour period, the organic solution containing the 10-deacetylbaccatin III was then purified by the following method. The reaction mixture was poured into 10 mL per gram of 50% by volume acetic acid/H$_2$O. The organic solution was then repeatedly extracted with an immiscible organic solvent, in this case glyme. The organic phase was collected and dried anhydrous sodium sulfate. The organic phase was then evaporated under vacuum to a viscous oil. The oil was purified by flash chromatography eluting with dichloromethane/5% methanol. The selected fractions were then evaporated to dryness under reduced pressure (20 mm Hg). The dry organic material was then recrystallized from methanol. 87 mg of 10-deacetylbaccatin III were recovered resulting in a 21% yield. The proton NMR and melting point of the product matched the previously reported literature values for 10-deacetylbaccatin III.

TABLE IIIb

| | |
|---|---|
| Reaction Solvent | glyme |
| with | NaBH$_4$/CoCl$_2$ pellets |
| Reaction temp (°C.) | room temperature |
| Reaction time | 144 hours |
| Theoretical yield 10-deacetylbaccatin III | 88 mg |
| Actual yield 10-deacetylbaccatin III (hplc) | 87 mg |
| % yield 10-deacetylbaccatin III | 21% |
| 10-deacetyltaxol remaining (hplc) | 41 mg |
| % 10-deacetyltaxol converted | 69% |

To determine without undue experimentation which Lewis acids will produce good yields of 10-deacetylbaccatin III from a mixture of partially purified taxanes, the following two step test must be analyzed. First, the Lewis acid should be able to covalently bond with strong nucleophilic species including, for example, oxygen anions. Thus, magnesium chloride will not be a preferred Lewis acid. Second, the Lewis acid must not react with the borohydride reducing salt to form boranes, e.g., B$_2$H$_6$. Lewis acids that can covalently bond with strong nucleophiles and do not react to form boranes can be used in the present invention. For example, Lewis acids such as SbCl$_5$, ZnCl$_2$, CuCl$_2$, PbCl$_2$, GeCl$_2$, SnBr₂, SnI₂ and CoBr₂ would be selected Lewis acids under the two step test.

Various experiments indicate that large scale production of 10-deacetylbaccatin III may require more than 0.1% of the Lewis acid. Furthermore, when large quantities of starting material are used it is extremely important to closely monitor the reaction by TLC and to be certain that the mixture is being well agitated so that the cleavage reaction can readily occur.

The present invention discloses new high yield processes for converting partially purified taxane mixtures into both baccatin III and 10-deacetylbaccatin III. These processes result in good yield of 10-deacetylbaccatin III which is essentially pure after further purification by methods known to those skilled in the art. Characterization of the resultant species confirms the structure of the resultant product to be 10-deacetylbaccatin III. In addition to the good yield of 10-deacetylbaccatin III these processes are commercially viable, inexpensive, and run at room temperature. The use of the borohydride reducing salts other than sodium borohydride and tetrabutylammonium borohydride and the use of other Lewis acids are contemplated by this invention.

Accordingly, the present invention has been described with some degree of particularity directed to the processes of the present invention. It should be appreciated, though, that the present invention is defined by the following claims construed in light of the prior art so that modifications or changes may be made to the processes of the present invention without departing from the inventive concepts contained herein. It is understood that the invention may be practiced otherwise than as specifically described.

We claim:

1. A process for the preparation of a compound of formula (I)

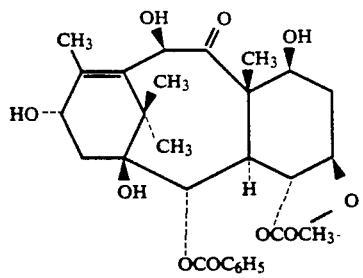

comprising contacting a mixture containing at least one taxane compound having an ester linkage at the C-13 position with at least one borohydride reducing salt in a reaction solvent in the presence of a Lewis acid.

2. The process of claim 1 wherein the borohydride reducing salt is sodium borohydride.

3. The process of claim 1 wherein the reaction solvent is selected from $CH_3(OCH_2CH_2)_xOCH_3$, where x is an integer from 1 to 5.

4. The process of claim 1 wherein the reaction solvent is tetrahydrofuran.

5. The process of claim 1 wherein the reaction solvent is dichloromethane.

6. The process of claim 1 wherein the Lewis acid is a metal halide.

7. The process of claim 6 wherein the metal halide is tin chloride.

8. The process of claim 6 wherein the metal halide is cobalt chloride.

9. A process for the preparation of a compound of formula (I)

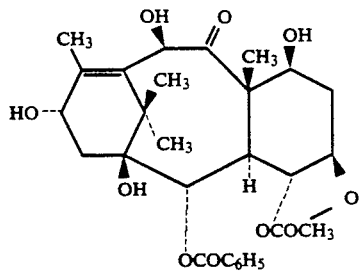

comprising contacting a mixture containing at least one taxane compound constituent having an ester linkage at the C-13 position with a borohydride reducing salt in triglyme.

10. The process according to claim 9 wherein said borohydride reducing salt is sodium borohydride.

11. The process according to claim 9 is conducted at a temperature of 22°–27° C.

* * * * *